(12) United States Patent
Huang et al.

(10) Patent No.: US 8,753,351 B2
(45) Date of Patent: *Jun. 17, 2014

(54) METHODS FOR REMOVING KIDNEY STONES FROM THE URETER

(75) Inventors: Alexander L. Huang, Menlo Park, CA (US); Rupesh Desai, San Jose, CA (US)

(73) Assignees: Percutaneous Systems, Inc., Palo Alto, CA (US); Takai Hospital Supply Co., Ltd., Tokyo (JP)

( * ) Notice: Subject to any disclaimer, the term of this patent is extended or adjusted under 35 U.S.C. 154(b) by 63 days.

This patent is subject to a terminal disclaimer.

(21) Appl. No.: 12/982,595

(22) Filed: Dec. 30, 2010

(65) Prior Publication Data

US 2011/0098690 A1    Apr. 28, 2011

Related U.S. Application Data

(63) Continuation of application No. 11/777,515, filed on Jul. 13, 2007, now Pat. No. 7,883,516, which is a continuation-in-part of application No. 10/886,886, filed on Jul. 7, 2004, now Pat. No. 7,462,183.

(51) Int. Cl.
*A61B 17/22* (2006.01)

(52) U.S. Cl.
USPC .......................................................... 606/127

(58) Field of Classification Search
USPC ................ 606/110, 113, 114, 127, 128
See application file for complete search history.

(56) References Cited

U.S. PATENT DOCUMENTS

| 2,756,752 A | 7/1956 | Scherlis |
| 4,030,406 A | 6/1977 | Wander et al. |
| 4,030,503 A | 6/1977 | Clark, III |
| 4,046,149 A | 9/1977 | Komiya |
| 4,262,677 A | 4/1981 | Bader |
| 4,295,464 A | 10/1981 | Shihata |
| 4,531,933 A | 7/1985 | Norton et al. |
| 4,706,671 A | 11/1987 | Weinrib |
| 4,762,130 A | 8/1988 | Fogarty |
| 4,807,626 A | 2/1989 | McGirr |
| 4,813,925 A | 3/1989 | Anderson, Jr. et al. |
| 4,930,496 A | 6/1990 | Bosley, Jr. |
| 5,011,488 A | 4/1991 | Ginsburg |

(Continued)

FOREIGN PATENT DOCUMENTS

| DE | 10031661 A1 | 1/2002 |
| EP | 0 605 427 B1 | 12/1992 |

(Continued)

OTHER PUBLICATIONS

Bard Urological Division Catalog, 1990, PA24, "Woven Blasucci Ureteral Catheters", 3 pages.

(Continued)

*Primary Examiner* — Ryan Severson

(74) *Attorney, Agent, or Firm* — Wilson Sonsini Goodrich & Rosati

(57) ABSTRACT

Occluding structures may be created within a body lumen by advancing a length of material distally through the body lumen. By drawing a distal location on the advanced length of material in a proximal direction, the material may be compacted into a structure which at least partially occludes the lumen. The occluding structure may be used to remove kidney stones from the ureter in conjunction with lithotripsy and irrigation.

9 Claims, 12 Drawing Sheets

(56) References Cited

U.S. PATENT DOCUMENTS

| | | | |
|---|---|---|---|
| 5,078,727 A | | 1/1992 | Hannam et al. |
| 5,135,534 A | | 8/1992 | Tulip |
| 5,192,286 A | * | 3/1993 | Phan et al. .................... 606/127 |
| 5,431,676 A | | 7/1995 | Dubrul et al. |
| 5,454,790 A | | 10/1995 | Dubrul |
| 5,531,717 A | | 7/1996 | Roberto et al. |
| 5,599,291 A | | 2/1997 | Balbierz et al. |
| 5,676,688 A | | 10/1997 | Jaker et al. |
| 5,681,274 A | | 10/1997 | Perkins et al. |
| 5,711,841 A | | 1/1998 | Jaker |
| 5,814,058 A | | 9/1998 | Carlson et al. |
| 5,836,913 A | | 11/1998 | Orth et al. |
| 5,860,972 A | * | 1/1999 | Hoang .......................... 606/2.5 |
| 5,879,366 A | | 3/1999 | Shaw et al. |
| 5,897,535 A | | 4/1999 | Feliziani et al. |
| 5,972,019 A | | 10/1999 | Engelson et al. |
| 5,989,264 A | | 11/1999 | Wright |
| 6,007,488 A | | 12/1999 | Jaker et al. |
| 6,080,174 A | | 6/2000 | Dubrul et al. |
| 6,214,037 B1 | | 4/2001 | Mitchell et al. |
| 6,240,968 B1 | | 6/2001 | Bigonzi-Jaker et al. |
| 6,325,812 B1 | | 12/2001 | Dubrul et al. |
| 6,494,893 B2 | | 12/2002 | Dubrul et al. |
| 6,500,185 B1 | | 12/2002 | Mathews et al. |
| 6,623,508 B2 | | 9/2003 | Shaw et al. |
| 6,656,146 B1 | | 12/2003 | Clayman et al. |
| 6,692,484 B1 | | 2/2004 | Karpiel et al. |
| 6,709,465 B2 | | 3/2004 | Mitchell et al. |
| 6,929,664 B2 | | 8/2005 | Kolb |
| 6,945,950 B2 | | 9/2005 | Clayman et al. |
| 7,214,229 B2 | | 5/2007 | Mitchell et al. |
| 7,217,250 B2 | | 5/2007 | Kolb |
| 7,316,663 B2 | | 1/2008 | Whitmore, III |
| 7,462,183 B2 | | 12/2008 | Behl et al. |
| 7,674,283 B2 | | 3/2010 | Mitchell et al. |
| 7,682,366 B2 | | 3/2010 | Sakurai et al. |
| 7,698,205 B2 | | 4/2010 | Romani |
| 7,879,066 B2 | | 2/2011 | Desai et al. |
| 7,883,516 B2 | | 2/2011 | Huang et al. |
| 2001/0044595 A1 | | 11/2001 | Reydel et al. |
| 2002/0183853 A1 | | 12/2002 | Mitchell et al. |
| 2003/0040754 A1 | | 2/2003 | Mitchell et al. |
| 2003/0050659 A1 | | 3/2003 | Murphy et al. |
| 2003/0078611 A1 | | 4/2003 | Hashiba et al. |
| 2003/0120281 A1 | | 6/2003 | Bates et al. |
| 2003/0153970 A1 | | 8/2003 | Rao et al. |
| 2003/0191492 A1 | | 10/2003 | Gellman et al. |
| 2003/0229332 A1 | | 12/2003 | Intoccia |
| 2004/0092956 A1 | | 5/2004 | Liddicoat et al. |
| 2004/0210239 A1 | | 10/2004 | Nash et al. |
| 2004/0220587 A1 | | 11/2004 | Teague et al. |
| 2005/0038447 A1 | | 2/2005 | Huffmaster |
| 2005/0060023 A1 | | 3/2005 | Mitchell et al. |
| 2005/0143678 A1 | | 6/2005 | Schwarz et al. |
| 2005/0197627 A1 | | 9/2005 | Huang et al. |
| 2005/0228481 A1 | | 10/2005 | Manasas et al. |
| 2006/0009784 A1 | | 1/2006 | Behl et al. |
| 2006/0116693 A1 | | 6/2006 | Weisenburgh et al. |
| 2007/0016244 A1 | | 1/2007 | Behl et al. |
| 2007/0088256 A1 | | 4/2007 | Intoccia |
| 2007/0191768 A1 | | 8/2007 | Kolb |
| 2009/0287238 A1 | | 11/2009 | Behl et al. |
| 2011/0172678 A1 | | 7/2011 | Behl et al. |
| 2013/0267990 A1 | | 10/2013 | Behl et al. |

FOREIGN PATENT DOCUMENTS

| | | |
|---|---|---|
| JP | 2001-507598 | 6/2001 |
| WO | WO 99/23952 | 5/1999 |
| WO | WO 2005/110244 A1 | 11/2005 |
| WO | WO 2006/014491 A2 | 2/2006 |
| WO | WO 2006/014491 A3 | 12/2007 |

OTHER PUBLICATIONS

Garrido et al., "Utilización del catéter "stone sweeper" en la patología litiásica del tracto urinario superior," [The use of Stone Sweeper catheter for stone disease of the upper urinary tract], Arch Esp Urol. Nov. 2006; 56(9):889-892. [English Abstract Only].

L'Esperance et al., "Ureteral Expanding Stent: A New Device for Urolithiasis," J Endourol. May 1, 2007; 21(5): 533-537.

Woitzik et al., "Polyethylene sheath device to reduce tumor cell seeding along the needle tract in percutaneous biopsy," (2003) Surg. Endosc. 17:311-314.

European seach report and search opinion dated Jul. 7, 2010 for EP 05770447.0.

International search report and written opinion dated Aug. 15, 2008 for PCT/US2007/069182.

International search report and written opinion dated Nov. 5, 2007 for PCT/US2005/023988.

Merriam-Webster definition of anchor as accessed on Jan. 31, 2013; http://www.merriam-webster.com/dictionary/anchor.

Merriam-Webster definition of surround as accessed on Jan. 31, 2013; http://www.merriam-webster.com/dictionary/surround.

Office action dated Feb. 8, 2013 for U.S. Appl. No. 13/073,680.

Office action dated Feb. 7, 2011 for U.S. Appl. No. 12/269,739.

Office action dated Apr. 14, 2008 for U.S. Appl. No. 10/886,886.

Office action dated May 25, 2010 for U.S. Appl. No. 11/777,515.

Office action dated Jul. 6, 2009 for U.S. Appl. No. 11/436,256.

Office action dated Jul. 22, 2010 for U.S. Appl. No. 11/436,256.

Office action dated Aug. 16, 2012 for U.S. Appl. No. 13/073,680.

Office action dated Sep. 15, 2010 for U.S. Appl. No. 12/269,739.

Office action dated Oct. 13, 2009 for U.S. Appl. No. 11/436,256.

Office action dated Nov. 9, 2009 for U.S. Appl. No. 11/777,515.

Office action dated Dec. 10, 2008 for U.S. Appl. No. 11/436,256.

European search report and search opinion dated Dec. 11, 2013 for EP 077975589.7.

Office action dated Oct. 9, 2013 for U.S. Appl. No. 13/907,705.

* cited by examiner

METHODS FOR REMOVING KIDNEY STONES FROM THE URETER

CROSS-REFERENCES TO RELATED APPLICATIONS

The present application is a continuation of application Ser. No. 11/777,515, filed on Jul. 13, 2007, which is a continuation-in-part of application Ser. No. 10/886,886, filed on Jul. 7, 2004, the full disclosure of which is incorporated herein by reference.

BACKGROUND OF THE INVENTION

1. Field of the Invention

The present invention relates generally to medical apparatus and methods. More particularly, the present invention relates to methods for removing kidney stones from the ureter.

It is common for kidney stones to pass from the kidney through the ureter to the urinary bladder. While muscular peristalsis of the ureter will often pass the stones into the bladder without complication, in some instances large and/or irregularly shaped stones may become lodged within the ureter causing discomfort and potential damage to the ureter and upper collective system.

A number of ways have been proposed for dislodging such kidney stones. For example, extracorporeal shock wave lithotripsy (ESWL) can be used to break up the kidney stones but is often ineffective when the stones are present in the ureter. Moreover, ESWL can produce irregularly-shaped fragments which, while smaller than the original stone, may have sharp edges that will prevent spontaneous passage of the particles through the ureter. In the case of a stone or fragment, impacted in the ureter, it is common practice to attempt capture, using a wire stone basket. The basket is introduced through a ureteroscope which itself is typically introduced retrograde through the urinary tract.

In many cases, further lithotripsy through the scope is performed (ISWL). It is often difficult to advance such stone baskets past the obstructing material. Attempts to pass wire baskets or other grasping apparatus past a stone lodged in the ureter also presents risk of damage to the ureter. Abrasion, stretching, or perforation of the ureter at the impaction site can cause local urine leakage or edema even if the stone or resulting debris is successfully captured; and removal of the basket with the stone may be quite difficult. In some instances, baskets containing captured stones or fragments cannot themselves be removed, and it is difficult if not impossible to release the captured stone material back into the lumen of the ureter. In those cases, the basket must often be retrieved surgically. Finally, if and/or when ISWL is performed, it would be useful to have some means of stabilizing stone fragments at the treatment site, rather than letting them escape up the ureter in a retrograde direction.

For these reasons, it would be desirable to provide improved methods and apparatus for capturing and removing kidney stones from the ureter. In particular, it would be desirable to provide methods for containing and managing stone fragments which are generated in a ureter as the result of applying energy from external or luminal sources. The methods and apparatus of the present invention should be generally atraumatic in use, require significantly less skill than basket manipulation, optionally allow the release of captured material, should be simple and economical in construction and use, and should provide minimum risk and trauma to the patient. At least some of these objectives will be met by the inventions described hereinbelow.

2. Description of the Background Art

The use of an everting sleeve composed of thin, tensilized polytetrafluoroethylene for introducing catheters to body lumens is described in U.S. Pat. Nos. 5,531,717; 5,676,688; 5,711,841; 5,897,535; 6,007,488; 6,240,968; and EP605427B1. A wire basket for advancing stone through a body lumen during lithotripsy procedure is available under the Stone Cone tradename from Boston Scientific Corporation. See Published U.S. Application No. 2003/0120281. Copending application Ser. No. 10/794,337, filed on Mar. 5, 2004, the full disclosure of which is incorporated herein by reference, describes a sheath delivery system that could be used in performing some of the methods described herein.

BRIEF SUMMARY OF THE INVENTION

The present invention provides methods for removing kidney stones from a ureter. The methods comprise occluding the ureter on the kidney or bladder side of the kidney stone, typically by compacting a length of material on that side of the stone to form an occluding structure. Energy is directed at the kidney stone to break the stone into fragments while the ureter remains occluded. The fragments will be irrigated, typically from an irrigation source directed towards the stone so that the irrigant flows through the fragments and then is diverted back by the occluding structure so that the stone fragments are dislodged and carried toward the bladder or kidney. Optionally, after the fragments have been irrigated and at least partially carried toward the bladder or kidney, the compacted length of material or other occluding structure may be drawn through the ureter to transport any remaining fragments out of the ureter.

While in some instances balloons, cages, or other structures which are generally impermeable to stone fragments and irrigant flow might be used as the occluding structure, it will be preferred to use the compacted length of material which has a number of advantages. The length of material will generally be relatively flexible or soft and will be atraumatic when it is compacted within the ureter. The compacted length of material will also conform to non-circular ureter geometries as well as to the irregular shape of the kidney stone prior to disruption. Additionally, the length of material can typically be drawn to a very narrow profile, thus facilitating introduction of the length of material past the kidney stone prior to compaction and enlargement. The ability to stretch and draw down the width of the material is also advantageous if it is desired to withdraw the occluding structure from the ureter and/or to release the stone or stone fragments which may have been captured in the compacted material. Such release is very difficult with a wire basket or similar structure.

The occluding structure typically comprises a length of material which is initially positioned in the body lumen in a generally elongate or unfurled configuration. The length of material is subsequently pulled, furled, or drawn back on itself so that the material compresses or compacts into the desired occluding structure. The material typically comprises a polymer film, a woven fabric, a non-woven fabric, and composites and laminates thereof. Exemplary polymer materials include polytetrafluoroethylene (PTFE), polyethylene (PE), perfluoroalkoxy (PFA), polyurethane (PU), perfluoromethylvinylether (MFA), and perfluoropropylvinylether (PPVE). Other exemplary materials include films, fabrics woven of any supple material such as nylon, polyester, silk, etc., lamination of these materials, and the like. The materials will generally be chosen so that they compress or compact into a relatively soft, non-traumatic mass of material. The compaction may be by folding, twisting, spiraling, or otherwise collapsing so that the length of the material becomes shorter and the width becomes greater, where length is a dimension generally aligned with the axis of the body lumen and width is the dimension generally transverse to the axis when the material is in the body lumen. In the exemplary embodiments, the length of material prior to compaction is in the range from 1 cm to 10 cm, usually from 2 cm to 6 cm, and most typically from 3 cm to 5 cm. The original length will be foreshortened so that the resulting compacted mass has a width that approximates the internal diameter of the lumen in the range from 1 mm to 10 mm, usually from 2 mm to 6 mm, and preferably from 3 mm to 5 mm.

By deploying the length of material in its elongated configuration, the material will have a very low profile which permits it to be advanced through narrow body lumens, and more particularly, past the kidney stones and other obstruction(s) which may be present. By then compacting the length of material on a distal side of the kidney stone, the compacted material may then be drawn in a proximal direction to form an occlusion which is drawn proximally in order to contain or move debris during lithotripsy. As discussed above, the debris can be released at any time by simply elongating the length of material to return to its non-compacted state.

In an exemplary embodiment, the length of material is advanced distally in the ureter and a distal location on the advanced length of material is drawn proximally to compact the material into a structure which at least partially occludes the ureter. Typically, the length of material is advanced distally past the stone in the body lumen and thereafter drawn proximally against the stone.

The length of material may be advanced in a variety of ways. For example, the length of material may be advanced or otherwise introduced through a tubular guide. In one instance, the tubular guide is first positioned through the body lumen and the length of material is advanced therethrough, typically using a separate advancement member. In a second instance, the tubular guide and the length of material are introduced simultaneously. Note that the tubular guide may subsequently be drawn proximally in order to expose an unsupported portion of the material. In a third instance, the length of material is advanced using an advancement member. The length of material is attached at or near a distal end of the advancement member, such as a guidewire, and the advancement member and length of material are simultaneously introduced through the body lumen and optionally past an obstruction. In a fourth and presently preferred instance, the tubular guide is introduced through the body lumen where a length of material is originally carried within the interior of the tubular guide. The length of material is everted over a distal end of the tube as the tube is introduced and acts as a barrier to protect the wall of the body lumen since the everted material will remain generally stationary relative to the wall. In the latter instance, the length of material is typically in the form of a sleeve which emerges from an interior lumen, passage, or receptacle of the tubular guide to cover an exterior of the tubular guide as the tubular guide is advanced and the sleeve everts.

In some instances, the tubular guide or other advancement member will also be used to draw back the advanced length of material proximally to compact the material into the occluding structure. In such instances, the systems used to perform the methods of the present invention may consist only of the length of material and the tubular guide or other advancement member. More usually, however, the systems of the present invention will include at least a third component which comprises a tension member for drawing proximally on the length of material after it has been advanced by the tubular guide or other advancement member. The tension member may have a wide variety of forms and may comprise suture, filament, a thread, a wire, a tube, or other elongate element that can be permanently or releasably attached to a distal location on the length of material. Frequently, the tension member will be woven, threaded, or otherwise incorporated into the length of material to facilitate the compaction of the material as the tension member is pulled backward. In an illustrated embodiment, the tension member is a filament which is woven in and out of axially spaced-apart locations on the length of material to permit folding of the length of material as the tension member is drawn proximally. The tension member could alternatively pass through loops or other attachment points on the length of material or could be woven in as part of the fabric of the length of material. Alternately, the tension member could pass through the lumen of a tubular sleeve of the material.

When using a separate tension member, the methods of the present invention will frequently comprise detaching the tension guide or other advancement member from the length of material prior to compacting the material. Alternatively, when using a tubular guide disposed within a sleeve-like length of material, the tubular guide may be partially withdrawn in a proximal direction leaving a distal portion of the length of material unsupported and ready for compaction. In many cases, it will be possible to reverse compaction of the length of material by distally advancing the tension member prior to detachment. For example, it may be desirable under certain circumstances to reverse compaction to release entrapped materials that cannot be removed. By releasing and recapturing, removal could be completed.

In certain embodiments, the length of material will comprise fold structures such as lines or other scored notched, or weakened regions or variations in thickness or geometry which impart a preferential folding pattern upon drawing the length of material in the proximal direction. Exemplary lengths of material may comprise strips, sleeves, ribbons, tubes, and the like, and preferred materials have been set forth above.

In a preferred method for introduction, a sleeve-like length of material is introduced using a tubular guide. The sleeve material is initially stowed within a central lumen or other passage or receptacle in the tubular guide. A first end of the sleeve is immobilized relative to an entry point into the body lumen being treated. The tubular guide is then advanced in a distal direction, and the length of material emerges from a distal end of the tube and everts so that the sleeve material covers the inner wall of the ureter. Thus, as the apparatus is introduced, the length of material acts as a protective barrier to reduce trauma to the wall of the ureter. It may further act to facilitate passage of the device past any stones or other obstructions which are present in the ureter. Pulling back on the tubular guide and/or the tension member with tubular guide in distal position will reverse advancement of the tubular guide. Finally, after the apparatus has been introduced a sufficient distance beyond any stone or other obstruction, the tubular guide may be withdrawn proximally from the sleeve until it is proximal to the obstruction. The sleeve can then be pulled back to provide the compacted material which is disposed adjacent the kidney stone. Pulling back the sleeve could be accomplished using the tubular guide, itself, but will more usually be accomplished using a separate tension member as described above.

DETAILED DESCRIPTION OF THE INVENTION

Figure 1:
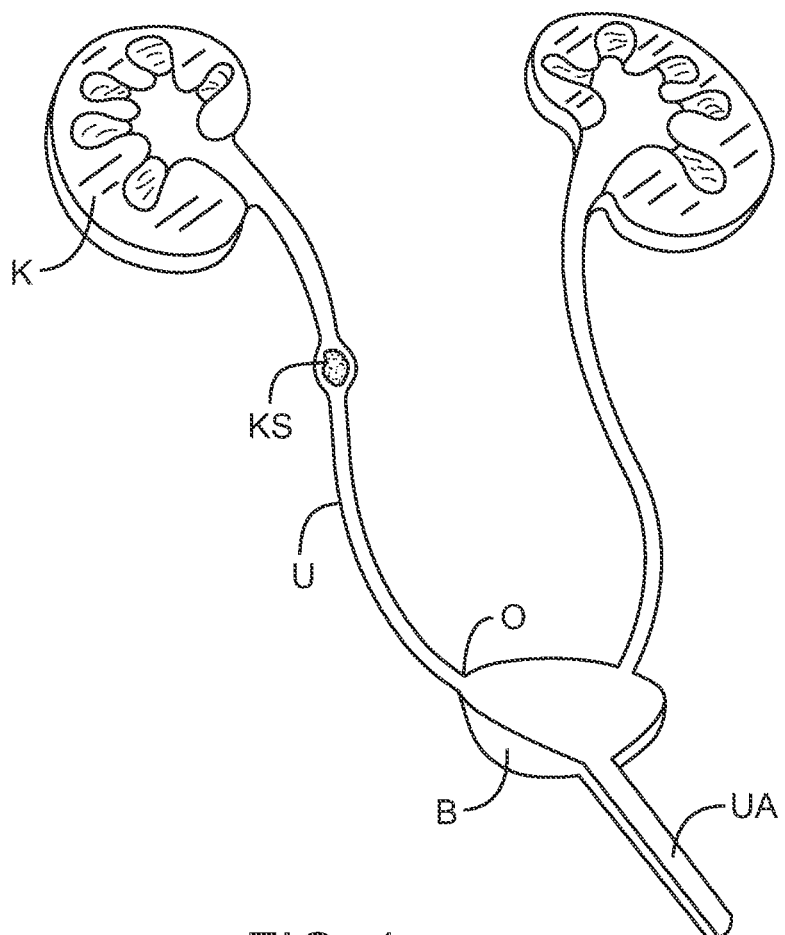
FIG. 1 illustrates a ureter having a kidney stone lodged between the kidney and bladder.

Referring now to FIG. 1, the present invention may be used for engaging, fragmenting, and retrieving a kidney stone KS or fragments from a ureter U between a kidney K and a bladder B. Access to the bladder will be through the urethra UA using conventional access devices which will not be described herein. Access to the ureter U will be through the os O in a wall of the bladder leading into the lumen of the ureter.

Figure 2A:
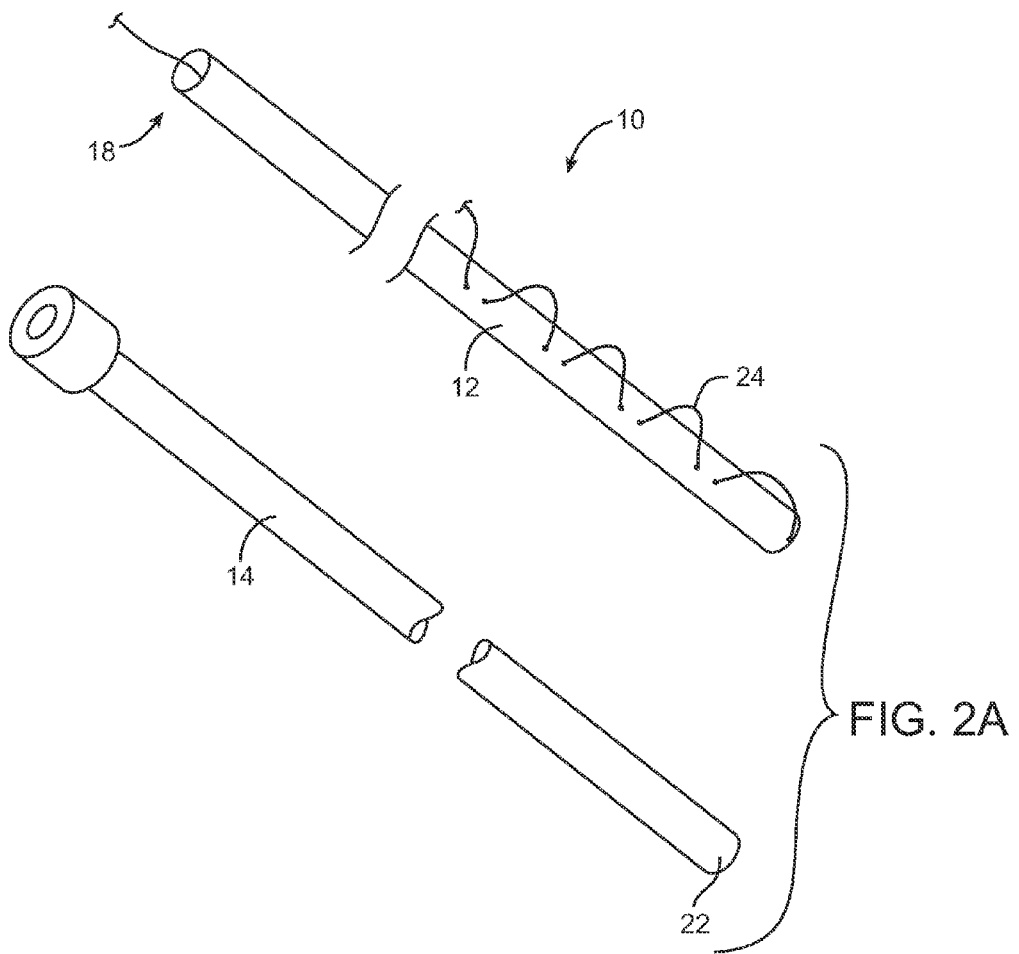
FIGS. 2A and 2B illustrate a first apparatus in accordance with the present invention which comprises a sleeve-like length of material, a tubular guide, and a tension member.
Figure 2B:
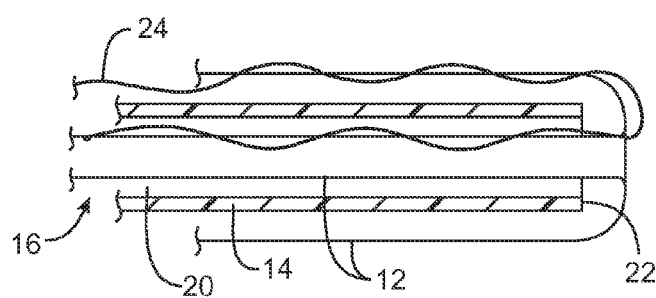

A first exemplary system 10 for performing the methods of the present invention comprises a sleeve-like length of material 12 and a tubular guide 14, as shown in FIGS. 2A and 2B. The sleeve-like length of material 12 has a trailing end 16 and an anchor end 18. The length of the sleeve-like length of material will typically be in the range from 1 cm to 10 cm, usually from 2 cm to 6 cm, although much longer lengths may find use in different circumstances. The sleeve will usually have a continuous sidewall with no openings (other than at the trailing end 16 and anchor end 18), but could also have open regions, have a loose weave in the case of woven materials, or otherwise have openings or discontinuities in the sidewall without departing from the principles of the present invention.

Referring now in particular to FIG. 2B, the sleeve-like length of material 12 may be arranged so that it is initially within a central passage 20 of the tubular guide 14. The material 12 can be arranged so that the anchor and 18 of the sleeve-like length of material 12 will initially be on the exterior of the tubular guide 14 and generally held stationary as the tubular guide is advanced. As the tubular guide 14 is advanced through the body lumen, the trailing end 16 is everted over the distal end 22 of the guide member, generally as shown in FIG. 2B. The trailing end 16 will usually include a tension member 24 which may be a suture, filament, thin wire, or other element which is attached at or near the terminus of the trailing end 16 and which preferably is woven and out of the material 12 over at least a portion of the length of material 12. Such woven or pleated structures will be described in more detail hereinbelow. Pulling on the tension member 24 will collapse and compact the length of material 12 in order to provide the desired luminal occlusion.

Referring now to FIGS. 3A-3J, use of the system 10 for removing a kidney stone KS from lumen L of a ureter U will be described. Initially, access is gained to the os O of the bladder B (FIG. 1) in a conventional manner. The tubular guide 14 will then be passed through the os O and into the lumen L of the ureter with the anchor end 18 of the sleeve-like member 12 being held stationary relative to the os. Specific systems for doing this are described in copending application Ser. No. 10/794,337, the full disclosure of which is incorporated herein by reference. A particular device for using a wire to advance and compact the length of material is described in copending application Ser. No. 11/777,522, filed on the same day as the present application.

Figure 3A:
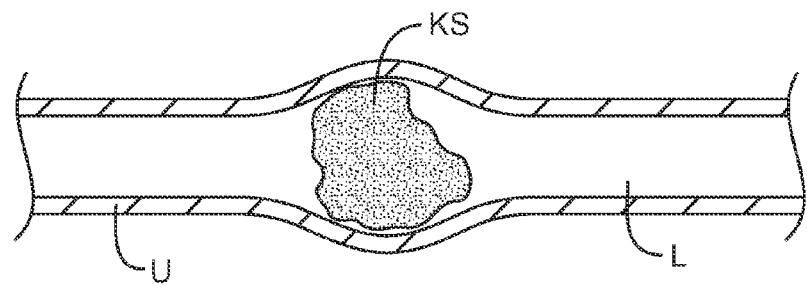
FIGS. 3A-3J illustrate use of the apparatus of FIGS. 2A and 2B for fragmenting and removing a kidney stone from a ureter.
Figure 3B:
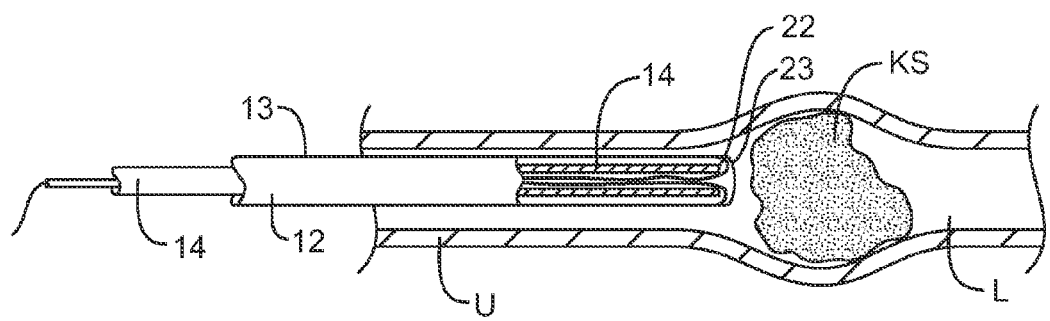
Figure 3C:
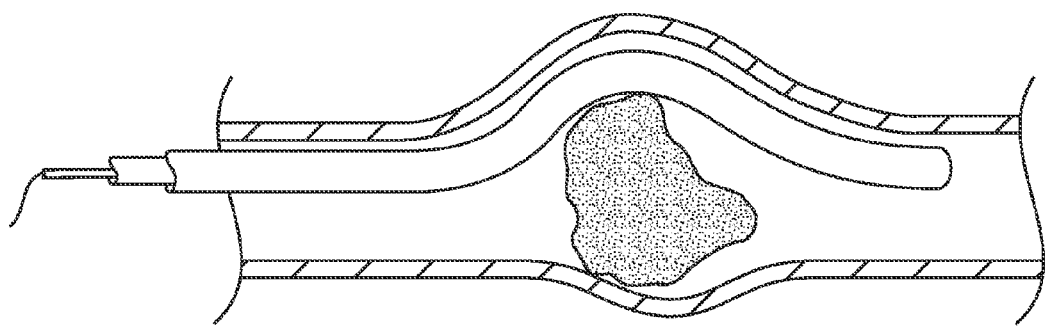

Referring now to FIG. 3B, the tubular guide 14 is advanced so that the sleeve-like length of material 12 everts from the distal end 22 of the guide. As the everting end 23 of the tubular guide 14 approaches the kidney stone KS, the sleeve-like length of material 12 will continue to be everted, but will have an exposed surface 13 which remains generally stationary relative to the inner wall of the ureter U and the exterior of the kidney stone KS. Such eversion of the sleeve-like length of material 12 acts like a "tractor tread" in allowing the tubular guide 12 to bypass the kidney stone, as illustrated in FIG. 3C. In addition to facilitating bypass of the kidney stone KS, the eversion of the length of material 12 also reduces the risk of perforation or other trauma to the ureter.

Figure 3D:
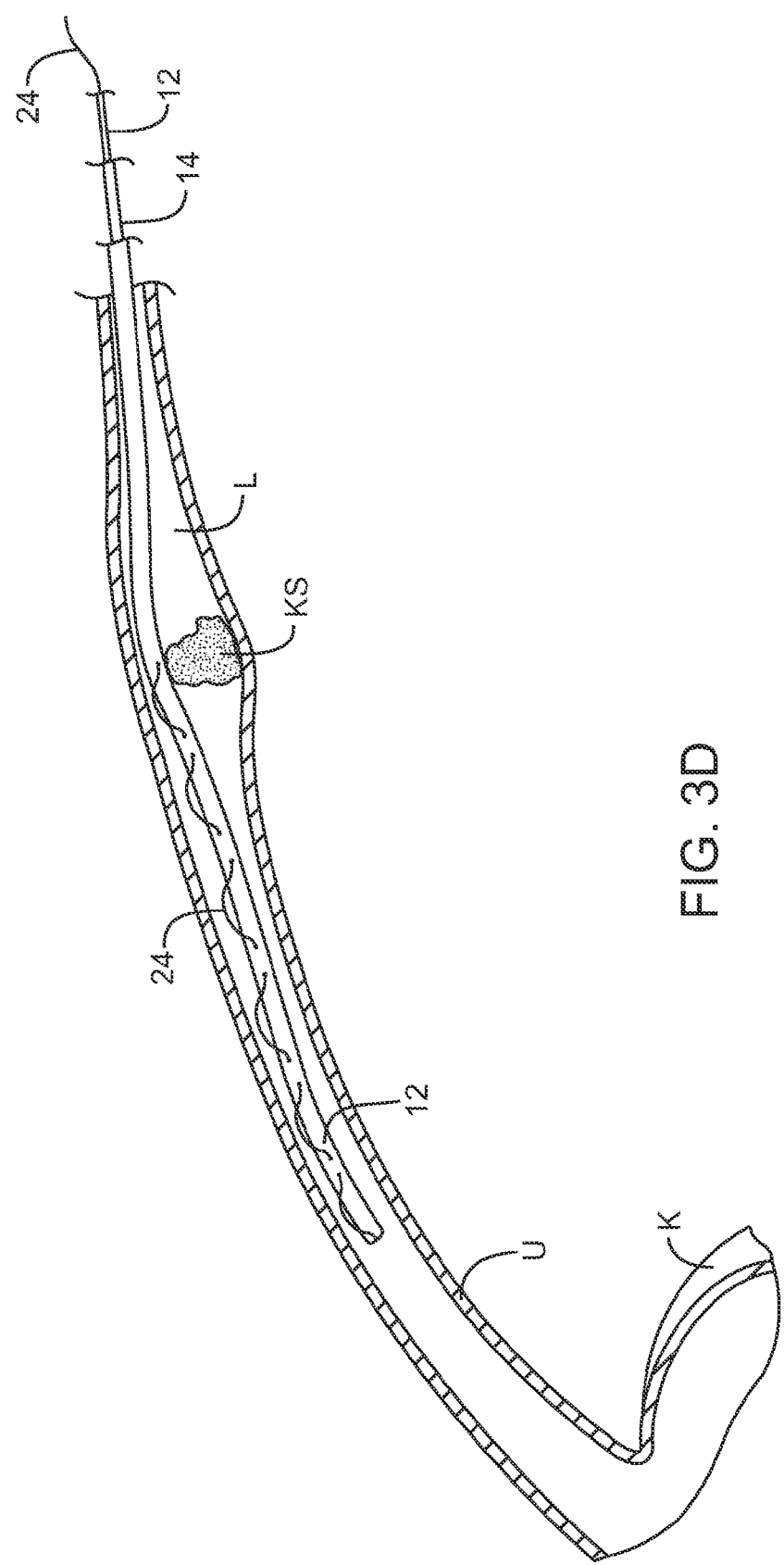

Referring now to FIG. 3D, once past the kidney stone KS, the tubular guide 14 will continue to be advanced through the lumen L in the distal direction (toward the kidney K) until the trailing end 16 has been partly or fully exposed so that the region including the tension member 24 lies distal to the kidney stone KS.

Figure 3E:
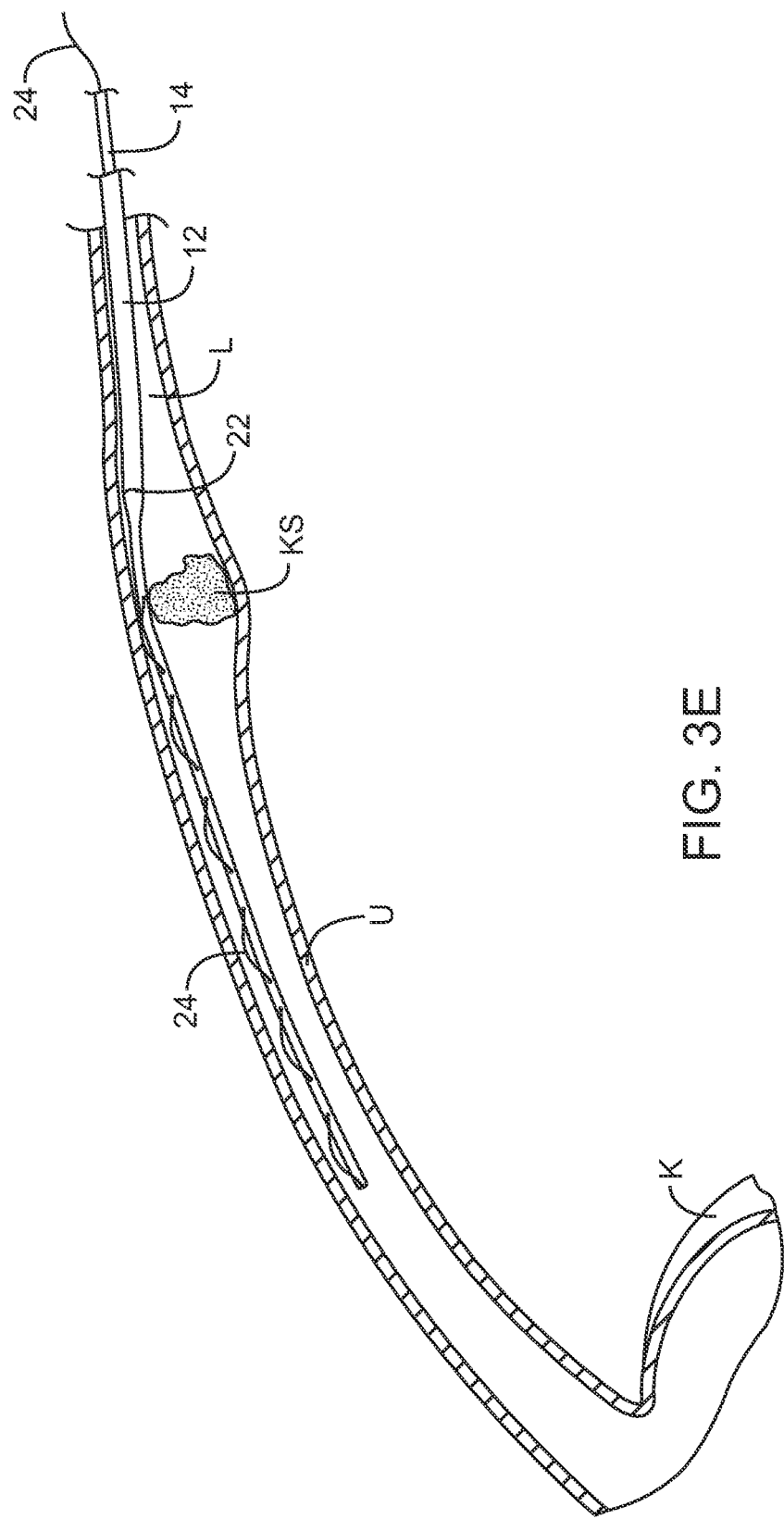
Figure 3F:
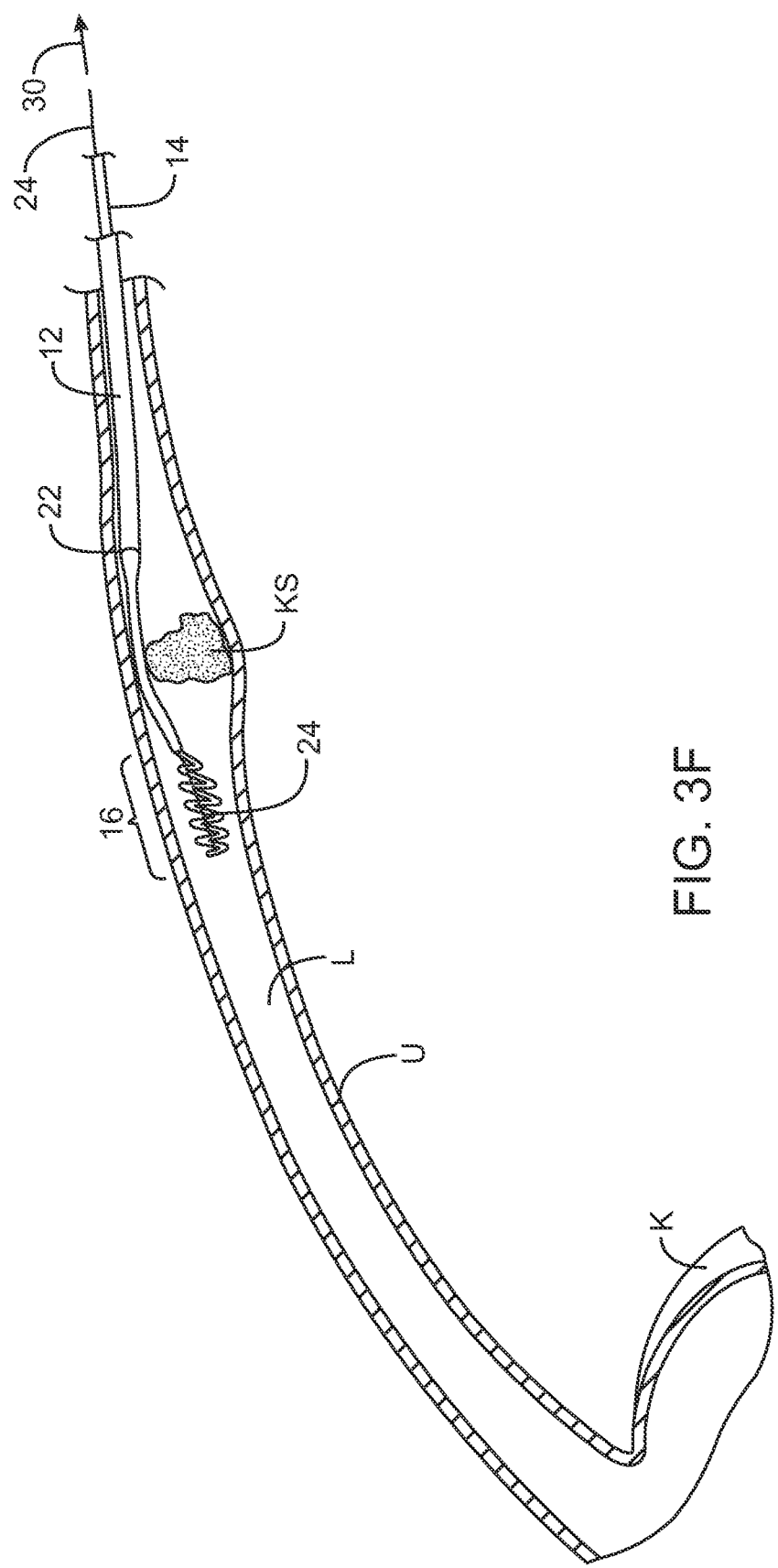
Figure 3G:
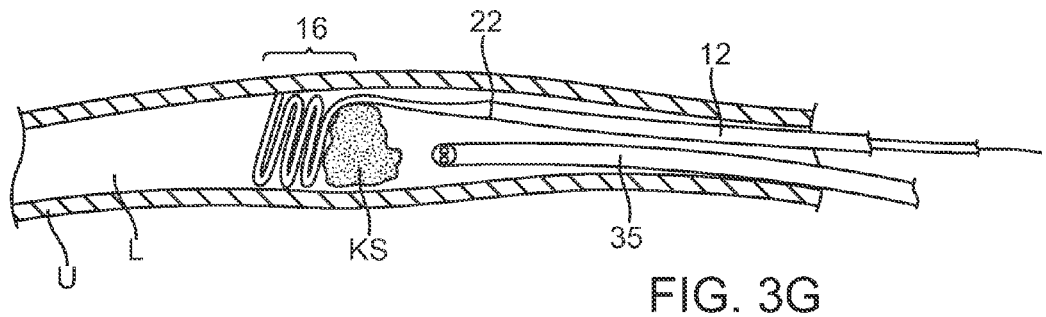

At this point, the tubular guide 14 will be at least partly withdrawn in a proximal direction so that its distal end 22 is located proximal of the kidney stone KS, as shown in FIG. 3E. The portion of the sleeve-like member 12 which lies distal to the kidney stone will radially collapse (since its internal support has been withdrawn) leaving a slack "shell" having the tension member 24 laced therethrough in place. By drawing in a proximal direction (arrow 30) on tension member 24, the trailing end 16 of the sleeve-like member 12 will be caused to axially collapse, generally in the manner of an accordion, as shown in FIG. 3F. By continuing to draw on the tension member 24 the trailing end 16 of the sleeve-like member 12 will be fully compacted against a distal surface of the kidney stone KS, as shown in FIG. 3G.

Figure 3H:
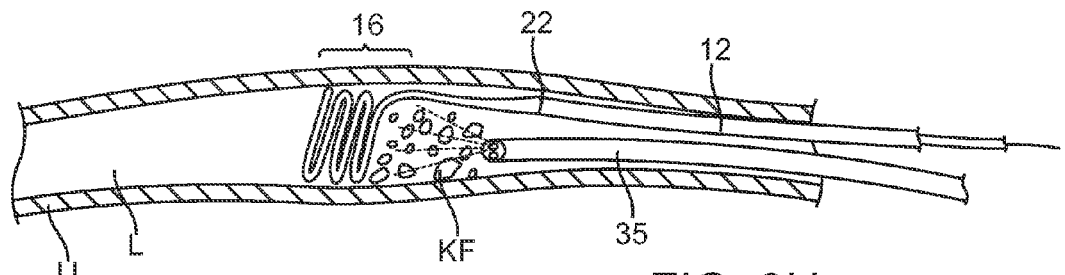
Figure 3I:
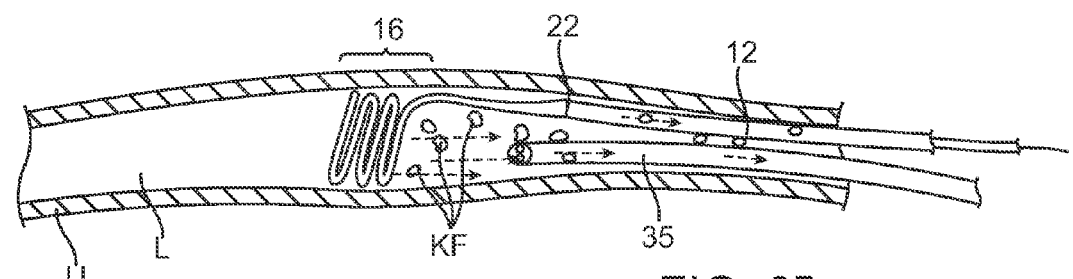
Figure 3J:
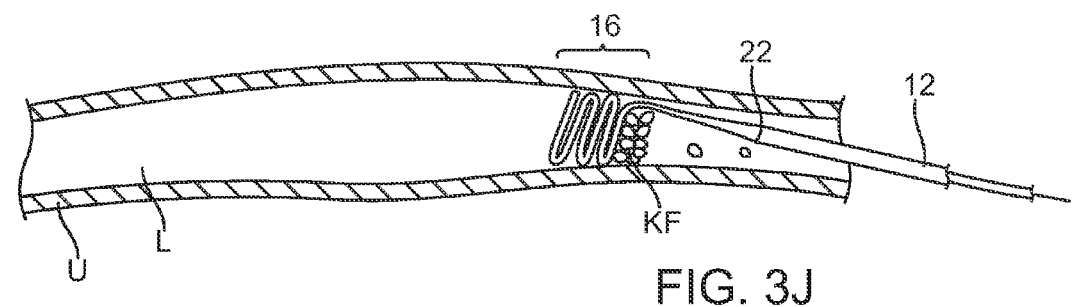

Once the kidney stone KS has been stabilized by the compacted material found in the trailing end 16 of the sleeve-like member 12, an energy-delivery device 35 will be introduced into the ureter U as generally described above. The energy-delivering device is typically delivered through a ureteroscope from below the stone (via the bladder), or a nephroscope from above (via the kidneys). Energy-delivering device 35 may be configured to deliver laser energy, ultrasonic energy, hydraulic shock energy, or any other type of energy which can fragment the kidney stone KS. The energy will be delivered to fragment the kidney stone into a plurality of fragments KF, as generally shown in FIG. 3H. During the time that the stone is being fragmented, an irrigant fluid will be introduced, typically through the same lumen in the ureteroscope or nephroscope which carries the energy delivery device 35, as shown in FIG. 3I. The irrigation fluid is typically introduced at a rate in the range from about 0.25 ml/sec to 1 ml/sec, but this rate is not critical. The irrigant fluid will flow toward the compacted trailing end 16 and will pass through the kidney stone fragments. Once the fluid engages the barrier formed by material 16, the fluid flow direction will reverse, since the obstruction formed by the compacted material is generally impervious or at least resistant to fluid flow therethrough. The reversed flow of the irrigant will carry at least some of the kidney stone fragments KF downstream toward the bladder or upstream toward the kidney, depending on the direction of introduction, while the compacted length of material 16 prevents migration or passage of fragments in the direction of irrigation. The ability to irrigate during fragmentation, without worry re. retropulsion of the stone or fragments, gives the physician a relatively clear view of the target stone/large fragments versus requiring him to work through an obscuring combination of blood and small stone fragments. Once the physician has reduced the stone/large fragments to an acceptable size, the compacted length of material 16 is drawn down toward the bladder in order to collect and remove any remaining kidney stone fragments KF, as shown in FIG. 3J. If the approach was from the kidney, the stone fragments may be withdrawn into the kidney and collected in a basket or by other conventional techniques. In some instances, it might be possible to redeploy the compacted length of material on the opposite side of the fragments and to use the compacted material to push the stone fragments out of the ureter.

Figure 4A:
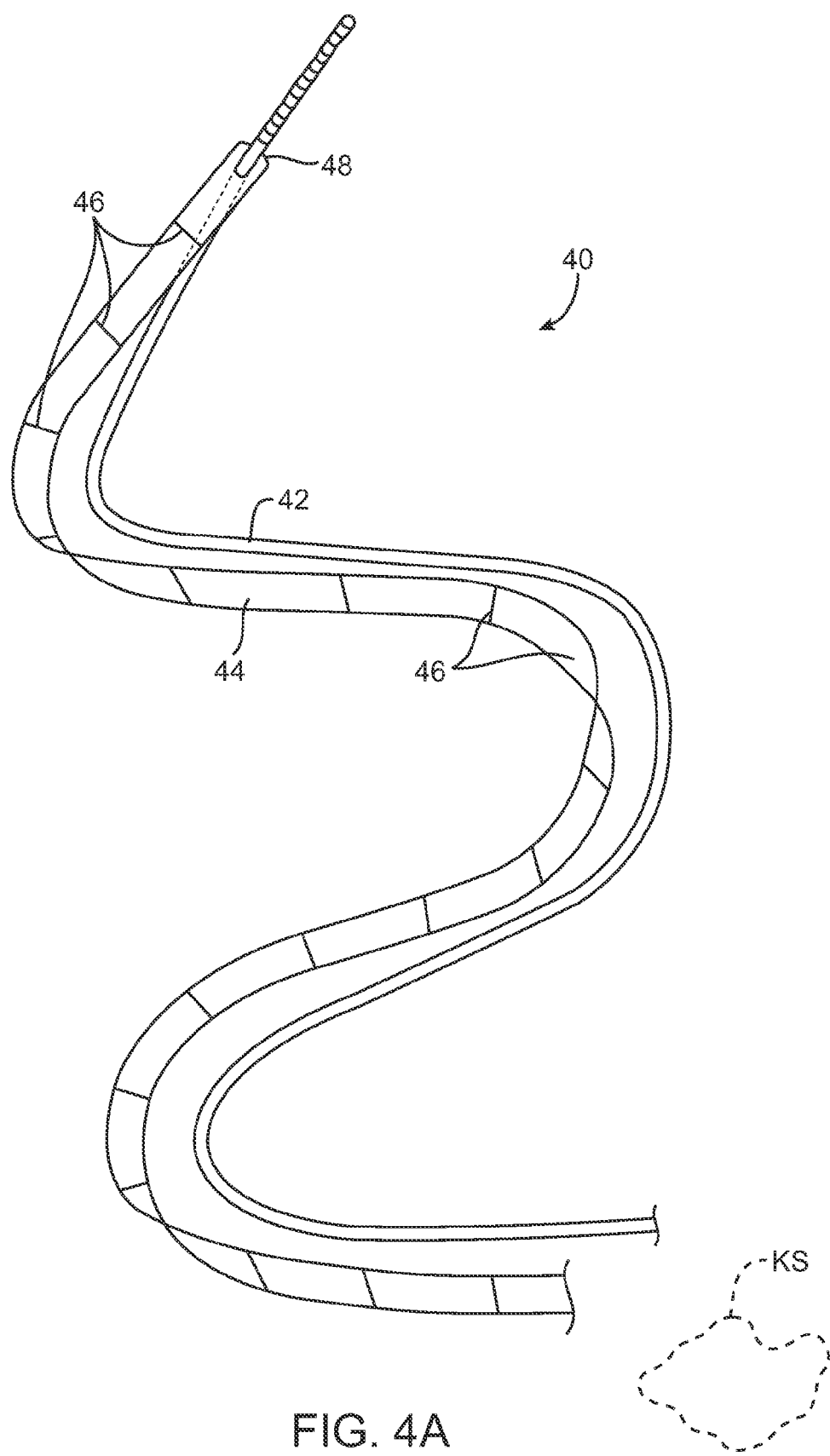
FIG. 4A illustrates a second apparatus useful for performing the methods constructed of the present invention comprising a length of material and a separate advancement member.
Figure 4B:
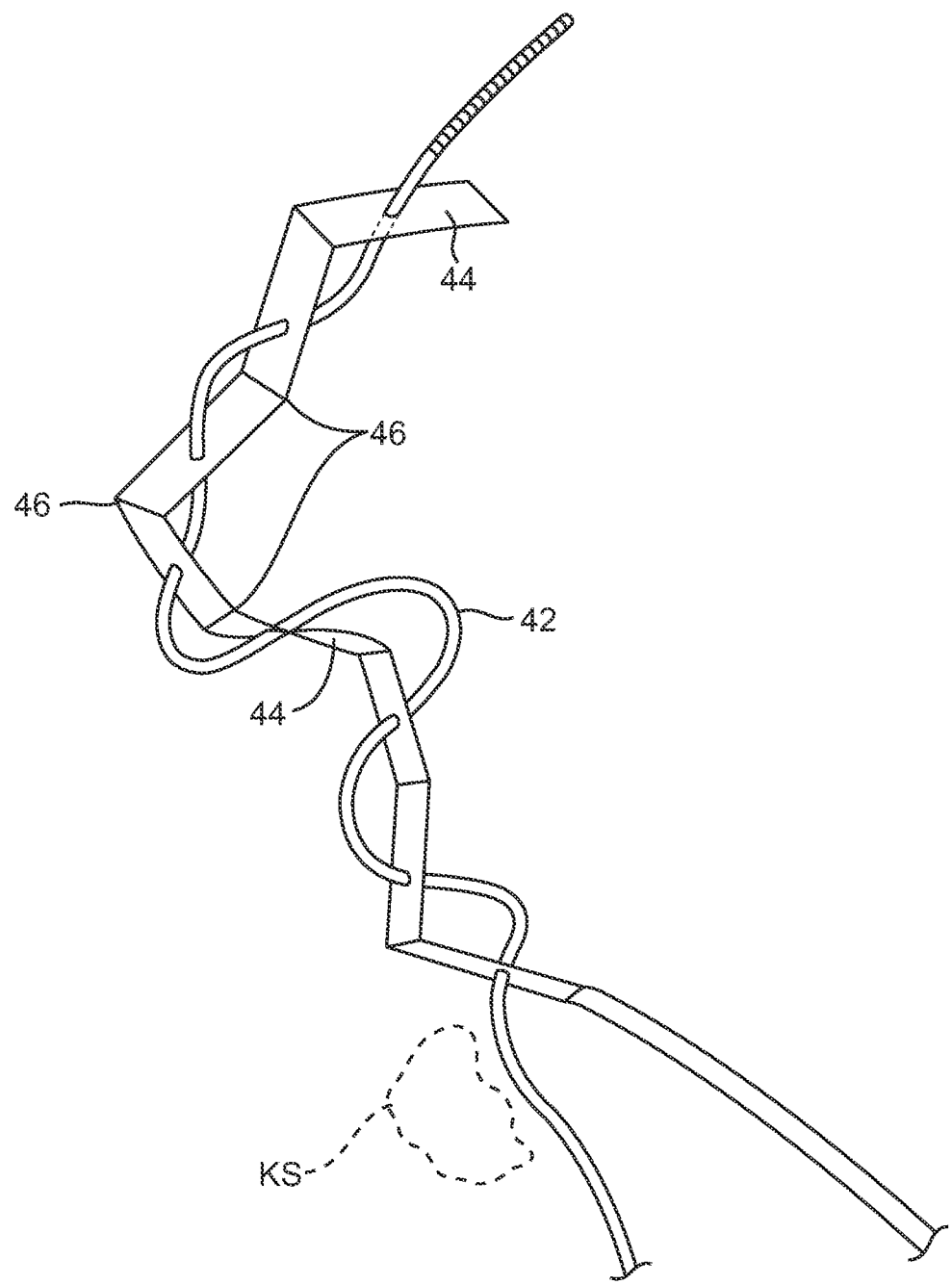
FIG. 4B illustrates a third apparatus similar to the second apparatus of FIG. 4A, except that the advancement member is threaded through a portion of the ribbon-like length of material.

Referring now to FIG. 4A, an alternative construction of an apparatus useful for performing the methods of the present invention will be described. System 40 comprises an advancement member 42 and a ribbon-like length of material 44. The advancement member may be a solid-core wire, a tube, or other small diameter or flat/thin member having sufficient column strength to permit its advancement through a body lumen and preferably past an obstruction, such as a kidney stone in a ureter. For example, the advancement member may be in the form of a guidewire of the type commonly used in urological procedures. The ribbon-like length of material 44 may be composed of any of the materials listed previously and may have a length in the ranges set forth above. The length of material 44 will typically consist of only a single layer with a width in the range from 1 mm to 10 mm, usually from 2 mm to 6 mm, and a thickness of 1 mm or less. Optionally, the ribbon-like length of material 44 will comprise a flattened tube or other multiple-layer or laminated structure instead of a single layer as illustrated. The ribbon-like length of material 44 may also have a plurality of axially spaced-apart fold structures 46 disposed over at least a distal length thereof. A distal end 48 of the length of material 44 will be attached at or near a distal end of the advancement member 42 so that the advancement member can pull or otherwise carry the ribbon-like length of material through the target body lumen as it is advanced. Optionally, as shown in FIG. 4B, the advancement member 42 can be penetrated or "laced" through axially spaced-apart locations on the ribbon-like length of material 44. As illustrated, the lacing occurs through consecutive sections defined by the fold structures 46. In both cases, the advancement member 42 will be used to advance at least a portion of the ribbon 44 past a stone KS or other object to be retrieved or stabilized.

Figure 5A:
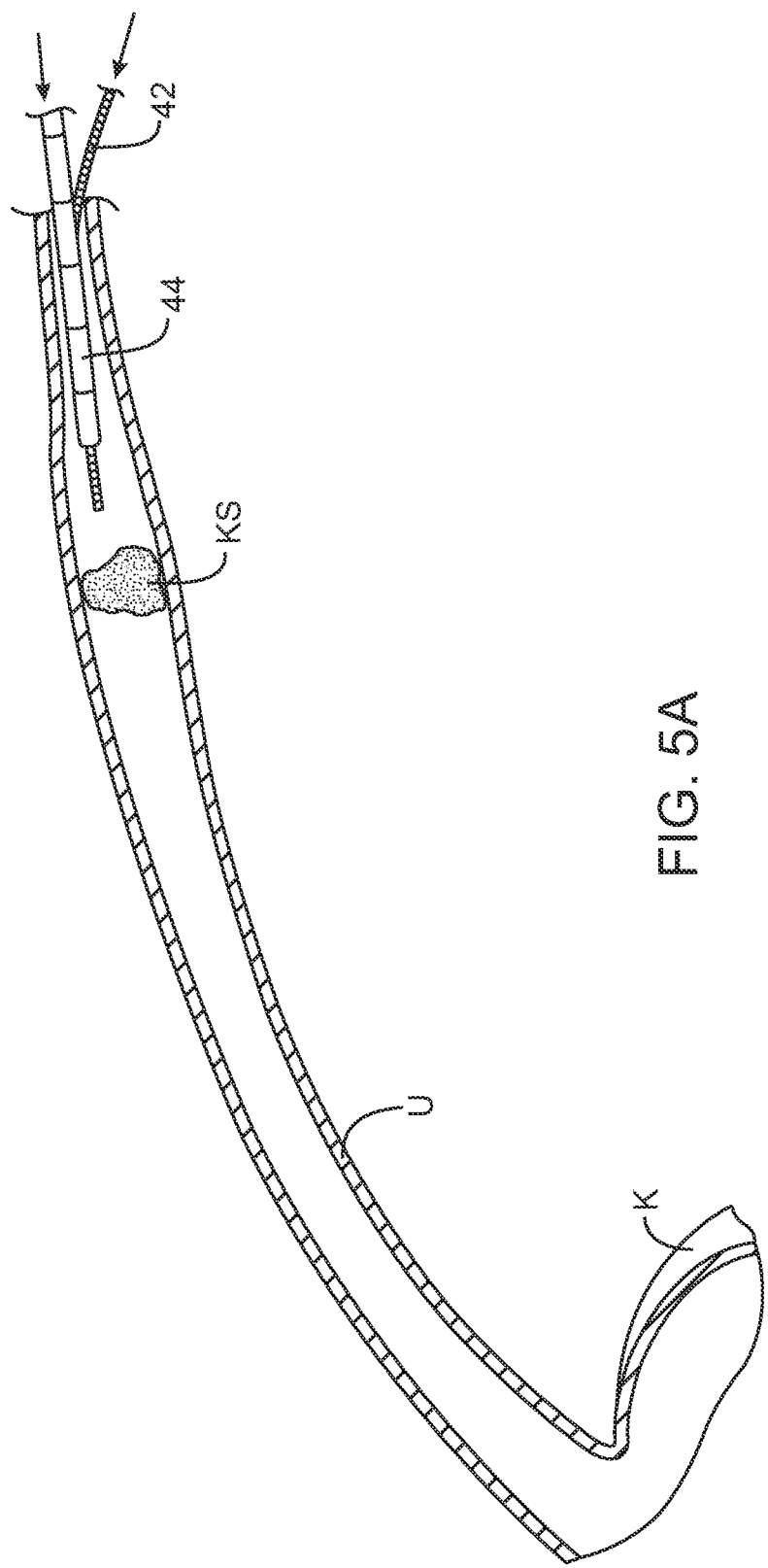
FIGS. 5A-5C illustrate use of the apparatus of FIG. 4A in accordance with the principles of the present invention.
Figure 5B:
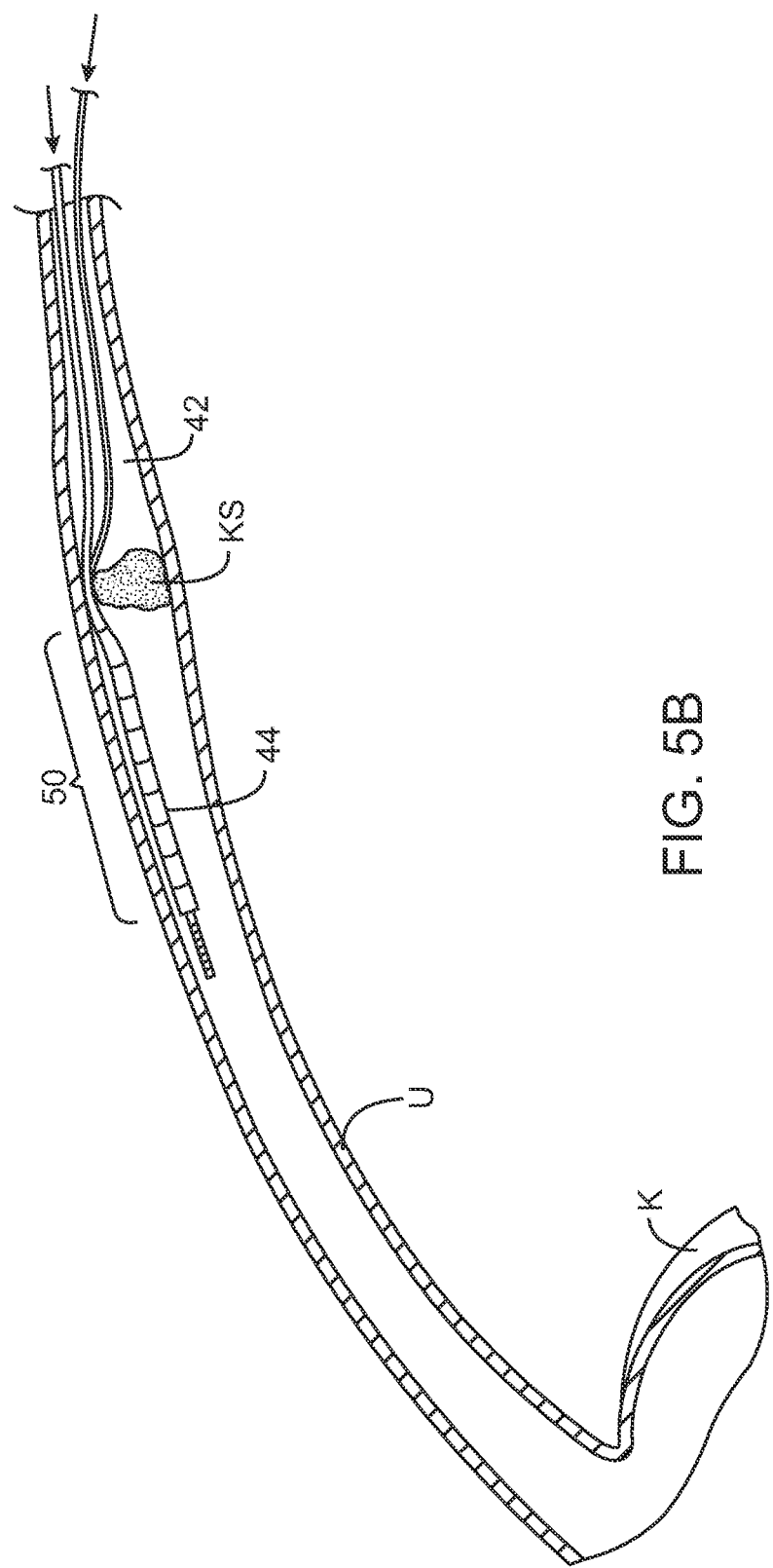
Figure 5C:
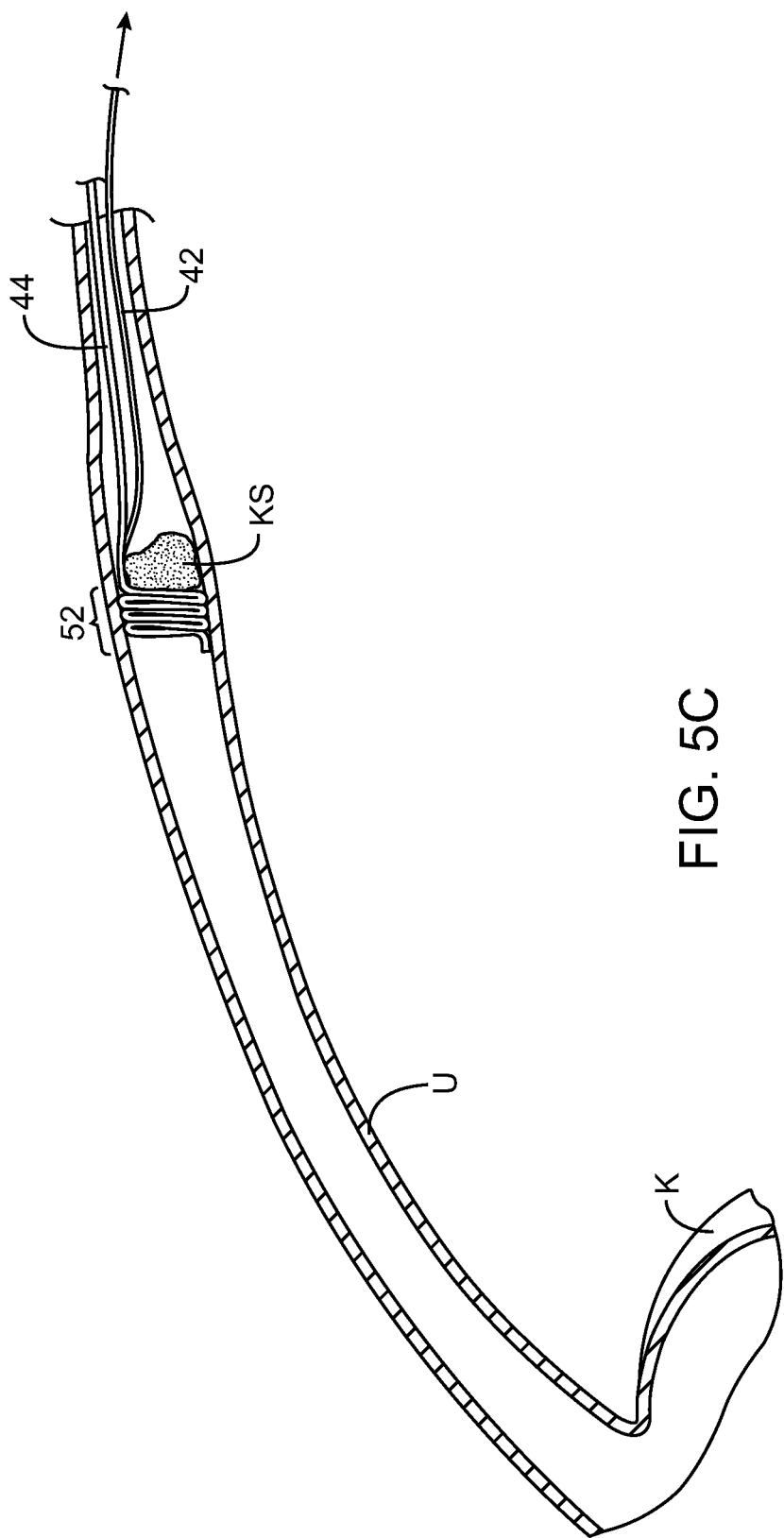

In use, the deployment system 40 of FIG. 4A is introduced by advancing advancement member 42 through the os O (FIG. 1) and into the lumen of the ureter U, as shown in FIG. 5A. The advancement member 42 carries the ribbon-like length of material 44 distally within the lumen and past the kidney stone KS as shown in FIG. 5B. After the desired distal positioning has been achieved, the advancement member 42 may be drawn in the proximal direction, as shown in FIG. 5C, while the proximal portion of the ribbon-like length of material 44 is left in place. In this way, a region 50 of the ribbon-like length of material 44 which is distal to the kidney stone KS, as shown in FIG. 5B, may be simultaneously or sequentially compacted into the foreshortened occluding structure 52, as shown in FIG. 5C. The compacted structure 52 may then be used as described previously, for moving and/or removing the kidney stone fragments into the bladder after lithotripsy.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for removing kidney stones from a ureter, said system comprising:
   a catheter adapted to be introduced into the ureter in a direction from a bladder toward a kidney, said catheter carrying a length of material that can be axially collapsed onto itself to compact the length of material on a kidney side of a kidney stone while a bladder side of the stone remains free from occlusion; and
   an energy delivery device adapted to be introduced into the ureter in a direction from the bladder toward the kidney and to deliver energy to fragment the kidney stone.

2. A system as in claim 1, wherein the catheter comprises an elongate member having a proximal end and a distal end, wherein the length of material has a proximal end and a distal end and the distal end of the length of material is attached to the distal end of the elongate member.

3. A system as in claim 2, wherein the length of material comprises a polymer film that can be pulled back on itself so that the material compacts into an occluding structure.

4. A system as in claim 3, wherein the polymer film is composed of a material selected from the group consisting of polytetrafluoroethylene (PTFE), polyethylene (PE), perfluoroalkoxy (PFA), polyurethane (PU), perfluoromethylvinylether (MFA), and perfluoropropylvinylether (PPVE).

5. A system as in claim 3, wherein the film has a length in the range from 1 cm to 10 cm when compacted.

6. A system as in claim 1, wherein the energy delivery device is configured to deliver laser energy, ultrasonic energy, or hydraulic shock energy.

7. A system as in claim 1, wherein the length of material can be axially collapsed onto itself in the manner of an accordion.

8. A system as in claim 1, wherein the length of material can be axially drawn to a narrow profile to reverse compaction and release entrapped material after compaction on the kidney side of the kidney stone.

9. A system as in claim 1, wherein the length of material comprises a flat polymeric film coupled at a distal end to a tension member that can be pulled proximally to axially collapse the flat polymeric film.

* * * * *